(12) United States Patent
Galmés Sureda et al.

(10) Patent No.: US 11,988,678 B2
(45) Date of Patent: *May 21, 2024

(54) TEST STRIPS FOR DETERMINING COAGULATION FACTOR ACTIVITIES

(71) Applicant: CGT Enterprises, LLC, Laguna Niguel, CA (US)

(72) Inventors: Bernat Galmés Sureda, Palma de Mallorca (ES); Mariana Isabel Canaro Hirnyk, Palma de Mallorca (ES); Vicente R. Cortina Giner, Palma de Mallorca (ES)

(73) Assignee: CGT ENTERPRISES, LLC, Laguna Niguel, CA (US)

( * ) Notice: Subject to any disclaimer, the term of this patent is extended or adjusted under 35 U.S.C. 154(b) by 162 days.

This patent is subject to a terminal disclaimer.

(21) Appl. No.: 17/187,460

(22) Filed: Feb. 26, 2021

(65) Prior Publication Data

US 2021/0293832 A1    Sep. 23, 2021

Related U.S. Application Data

(63) Continuation of application No. 16/550,767, filed on Aug. 26, 2019, now Pat. No. 10,969,397, which is a
(Continued)

(30) Foreign Application Priority Data

May 14, 2013    (ES) ................. ES201330983

(51) Int. Cl.
    *B01L 3/00*      (2006.01)
    *C12Q 1/56*      (2006.01)
    *G01N 33/86*     (2006.01)

(52) U.S. Cl.
    CPC .............. *G01N 33/86* (2013.01); *B01L 3/502* (2013.01); *C12Q 1/56* (2013.01); *B01L 3/5027* (2013.01);
(Continued)

(58) Field of Classification Search
    CPC ....................................... B01L 3/502
    See application file for complete search history.

(56) References Cited

U.S. PATENT DOCUMENTS 5,601,995 A    2/1997    Exner
9,651,567 B2   5/2017    Galmes Sureda
(Continued)

FOREIGN PATENT DOCUMENTS

EP    1462122 A1    9/2004
EP    1769735 A1    4/2007
(Continued)

OTHER PUBLICATIONS

European Patent Application No. 14705782.2 Communication dated Mar. 9, 2017.
(Continued)

*Primary Examiner* — Rosanne Kosson
(74) *Attorney, Agent, or Firm* — WILSON SONSINI GOODRICH & ROSATI (57) ABSTRACT

Test strips for determining the activity of a coagulation factor in a blood sample are provided. The strip comprises a support, a sample inlet port for deposition of a blood sample, and a reaction area comprising a blood coagulation reagent. The sample inlet port is connected to the reaction area, and the coagulation reagent comprises blood plasma deficient in the coagulation factor for which activity is to be measured, an ionic citrate source an ionic calcium source, and either one or more coagulation contact phase activator reagents and phospholipids or a mixture of tissue factor and
(Continued)

phospholipids. The disclosure further relates to in vitro methods for measuring an activity of a coagulation factor.

25 Claims, 3 Drawing Sheets

Related U.S. Application Data continuation of application No. 15/483,876, filed on Apr. 10, 2017, now Pat. No. 10,436,805, which is a continuation of application No. 14/891,119, filed as application No. PCT/EP2014/053461 on Feb. 21, 2014, now Pat. No. 9,651,567.

(52) U.S. Cl.
CPC . *B01L 2300/024* (2013.01); *B01L 2300/0825* (2013.01); *B01L 2300/0838* (2013.01); *B01L 2300/0864* (2013.01); *G01N 2333/7454* (2013.01)

(56) References Cited

U.S. PATENT DOCUMENTS

| | | | |
|---|---|---|---|
| 10,436,805 B2 | 10/2019 | Galmes Sureda et al. | |
| 10,969,397 B2 | 4/2021 | Galmes Sureda et al. | |
| 2006/0115868 A1 | 6/2006 | Hubbard | |
| 2007/0289880 A1 | 12/2007 | Zweig et al. | |
| 2011/0217284 A1 | 9/2011 | Seifried et al. | |

FOREIGN PATENT DOCUMENTS

| | | |
|---|---|---|
| EP | 2201365 B1 | 4/2011 |
| EP | 2997156 A1 | 3/2016 |
| WO | WO-9013034 A1 | 11/1990 |
| WO | WO-9720066 A1 | 6/1997 |
| WO | WO-9724604 A1 | 7/1997 |
| WO | WO-0144819 A2 | 6/2001 |
| WO | WO-2007040925 A1 | 4/2007 |
| WO | WO-2014183886 A1 | 11/2014 |

OTHER PUBLICATIONS

European Patent Application No. 18169019.9 Examination Report dated Sep. 30, 2020.
Hemochron® Jr. Signature+ Whole Blood Microcoagulation System, Operator's Manual, English, ITC, Edison, NJ, 2004, 52 pages. retrieved at: http://www.accriva.com/uploads/literature/hj7006_1004.pdf.
Kessler et al. in "Bedside measurement of Factor VIII:C Activity in Individuals With Hemophilia", American Journal of Hematology, 51:181-185, 1996.
PCT/EP2014/053461 International Preliminary Report on Patentability dated Nov. 17, 2015.
PCT/EP2014/053461 International Search Report and Written Opinion dated Apr. 15, 2014.
Poller et al., "A comparison of lyophilized artificially depleted plasmas and lyophilized plasmas from patients receiving warfarin in correcting for coagulometer effects on international normalized ratios", Am J Clin Pathology, 103(3):366-371, 1995.
Ruszicka et al., "Evaluation of Bedside Prothrombin Time and Activated Partial Thromboplastin Time Measurement by Coagulation Analyzer Coagucheck Plus® in Various Clinical Settings", Thrombosis Research , 87(5):431-440, 1997.
U.S. Appl. No. 14/891,119 Restriction Requirement dated Oct. 21, 2016.

TEST STRIPS FOR DETERMINING COAGULATION FACTOR ACTIVITIES

CROSS-REFERENCE

This application is a continuation of U.S. application Ser. No. 16/550,767, filed on Aug. 26, 2019, which is a continuation of U.S. application Ser. No. 15/483,876, filed on Apr. 10, 2017 (now U.S. Pat. No. 10,436,805, issued Oct. 8, 2019), which is a continuation of U.S. application Ser. No. 14/891,119, filed on Nov. 13, 2015 (now U.S. Pat. No. 9,651,567, issued May 16, 2017), which is a U.S. National Phase Application of International Application No. PCT/EP2014/053461, filed Feb. 21, 2014, which claims the benefit under 35 U.S.C. 119(b) of Spain (ES) Appl. No. P 201330983, filed May 14, 2013, each of which is incorporated by reference herein in its entirety.

The present invention relates to the field of blood parameters analysis and in particular to devices and tools for determining coagulation factor activities. Thus, it relates to the field of medicine, diagnosis, as well as to tools and machines adapted to take measures in blood samples.

The following definitions are included herein merely for the purposes of enhancing the understanding of the invention described herein.

The term "blood coagulation reagent" as defined herein, relates to a compound or group of compounds, as well as to mixtures of compositions that allow coagulation of a blood sample alone or in combination with other reagents, said other reagents commonly being ionic calcium source (i.e., organic and inorganic calcium salts), as well as plasmas artificially depleted in any of the coagulation factors; coagulation contact phase activators, mixtures of tissue factor and phospholipids, and control samples including either blood or plasma comprising known amounts of any of the coagulation factors and covering factor activities considered both normal and pathologic values, according to commonly accepted reference ranges in haematology.

The term "coagulation contact phase activator" or "surface contact activators" (herein used interchangeably) relates to any compound that promotes activation of the intrinsic coagulation pathway by surface contact. This intrinsic pathway is also referred to as contact activation pathway. The contact activation pathway begins with formation of the primary complex on collagen by high-molecular-weight kininogen (HMWK), prekallikrein, and FXII (Hageman factor). Prekallikrein is converted to kallikrein and FXII becomes FXIIa. FXIIa converts FXI into FXIa. Factor XIa activates FIX, which with its co-factor FVIIIa forms the tenase complex, which activates FX to FXa. The minor role that the contact activation pathway has in initiating clot formation can be illustrated by the fact that patients with severe deficiencies of FXII, HMWK, and prekallikrein do not have a bleeding disorder. Instead, the contact activation system seems to be more involved in inflammations. Examples of contact phase activators include, thus, any of the natural compounds or complexes formed with collagen, HMWK, and prekallikrein.

Other examples of contact phase activators include artificial compounds of polyanionic nature, such as kaolin of general formula $Al_2Si_2O_5(OH)_4$, and other silicates, or organic acids, such as ellagic acid. These compounds are indeed mimics of cell surfaces or of tissue surfaces.

A "factor depleted plasma" refers to plasma usually from an artificial origin from which one or more target proteins have been removed, for example, by means of selective affinity immune-adsorption technologies or e.g. chemically. Generally, they are human citrated plasmas and they may be deficient plasmas in any of the following factors: II, V, VII, X, VIII, IX, XI, XII.

The expression "low levels of the coagulation factor to be measured" is to be understood as that the composition (i.e. plasma) has an amount of a specified coagulation factor lower than the amount considered as normal according to commonly accepted laboratory reference ranges. The amount of a particular coagulation factor in plasma can be determined both by non-functional (antigen) and functional (factor activity) means; both measures must not necessarily coincide and can be expressed as a percentage referred to by a primary international standard established by the World Health Organisation (WHO). Focusing on factor activities, the factor present in a particular sample can be measured by comparing the value of some of the specific physical property that will vary as the clot is forming (which in turn will depend on the particular kind of assay used in the laboratory to determine the amount of factor, i.e. chromogenic, optical, electrical, etc) with those of a calibration graph obtained from a calibrator with a known factor activity percentage referred to the WHO primary standard properly diluted to yield several calibration points and covering a factor activity percentage range broad enough to determine either normal and pathologic values, so that a particular variation in the physical property used to draft the calibration curve can be converted in a percentage of factor activity. Obviously, sample measures must be based on the same physical property, reagents, equipment and general procedure followed in the case of the calibration curve. Normal amounts of coagulation factors are those defined by a range of values including the values usually found in normal subjects. It is widely accepted that normal amounts (activities) may vary depending on the specific assay, reagents, equipment and procedure used to determine factor activities, among races and populations within said races, among the people with different blood groups, and so do the activity values of the coagulation factors. This is why the value of any of the coagulation factor activity varying typically from 70% to 150% could be considered normal. In the present description the expressions "amount/level of a coagulation factors" and "activity of a coagulation factor" are considered synonymous, because independently of the determination (non-functional vs. functional) one correlates with the other On the other hand, it is also widely accepted that a value of any of the coagulation factor activity varying from 40% to 70% is to be considered as non-normal but also non-pathologic; and that a value of any of the coagulation factor activity varying from 0% to 40% is considered non-normal and pathologic. A "pathological coagulation factor deficiency" refers to a deficiency degree of a particular factor implying a disease and/or with severe consequences for the maintenance of life.

Ranges given, such as activities of coagulation factors, temperatures, times, sizes, and the like, should be considered approximate, unless specifically stated. The expression "between XX and YY" is considered equivalent to the expression "from XX to YY".

BACKGROUND ART

In the field of blood coagulation, it is known to determine the parameters known as Activated Partial Thromboplastin Time (APTT) and/or the Prothrombin Time (PT). Both parameters give a value indicating the time required for blood coagulation. In principle, these measures do not require any specialized personnel or special equipment and they can be determined in hospitals or non-specialized laboratories. Moreover, particular devices exist, even Point of Care (POC) devices for determining these parameters in the hospitals or at home.

Examples of these devices include the CoaguCheck Plus® (CCP®) commercially available from e.g. Boehringer Mannheim. It is a battery powered, portable laser photometer with APTT reagents (for intrinsic pathway coagulation) and PT reagents (for extrinsic pathway coagulation). The reagents are disposed in a wafer-like disposable plastic reagent cartridge/strip. A sample of whole blood is applied to an application well in the cartridge and blood flows through capillary action to the reagent chamber.

Coagulation starts when the blood of the sample comes into contact with the reagents and is considered to have stopped when the photometer detects cessation of blood flow. The detection is based on sensing the variation in light scatter from red cells. The time between blood application and blood clotting is measured and converted to the plasma equivalents APTT or PT.

The document WO9013034 discloses a test strip comprising an orifice or area adapted to receive a sample of whole blood, a capillary track leading the sample to a zone comprising the reagents for initiating coagulation and for the in situ measure of APTT. The strip is also provided with a venting port. The aim of the device is the determination of blood flow stoppage independently of the blood haematocrit, which has been reported as an inconvenient in test strips using blood samples as fluid test.

Determination of APTT or PT, as well as of other blood parameters, is of great relevance for patients receiving anti-coagulant treatments. In the same way, coagulation time is a critical aspect in intensive care units for the monitoring of heparin treatment and in preoperative assessment of blood coagulation. As a general rule, APTT or PT may be easily determined in normal conditions, which means that the subject (patient) does not have any inherited or acquired coagulation factor deficiency. APTT and/or PT may be altered when the subject has a coagulation factor deficiency, making further diagnostic tests necessary. In these scenarios patients are redirected to more specialized hospitals or analytical laboratories, which elongate the diagnosis time. This also supposes an uncomfortable procedure for the patient. Another disadvantage is that relatively high amount of blood (namely the further processed plasma) may be required.

The standardised mode to measure the deficiency of one or more coagulation factors can be summarized as follows. A plasma test sample is firstly diluted with a buffer, and then mixed with factor depleted-plasma which is deficient only in the coagulation factor that is going to be detected in the test sample, and comprising all other coagulation factors. Next, reagents either from the extrinsic or intrinsic coagulation pathway needed to start coagulation are added to the mixture. Coagulation is then only dependent on the limiting coagulation factor, corresponding to the one being measured in the test sample. A modification of this standardised method is in particular disclosed for factor V activity in the document WO9720066. The document WO9720066 discloses the way for determining if a patient is susceptible of suffering a thromboembolism. Analysis is performed using plasma and determining the ratio between factor V activity level without activated protein C (APC) and the factor V activity level with APC. Factor V depleted plasma is added to increase the specificity of the test.

Among the commercial tests adapted for detecting coagulation factor deficiencies, the test known as Actin FS® from Baxter Diagnostics Inc. is one of the multiple examples commonly used in the specialized laboratories to test coagulation factor activities in plasma samples. The test includes all the reagents for an APTT determination (purified soy phosphatides, ellagic acid activator and calcium) in liquid form and ready for use. It allows analyzing factor defects of factors VIII, IX, XI, and XII with high sensitivity and specificity.

As above exposed all these test are performed on plasma and require venous blood samples.

It is an object of the present invention to provide methods and devices that at least partially solve one or more of the aforementioned problems.

SUMMARY

In a first aspect, a test strip for determining the activity of a coagulation factor in a blood sample is provided. The strip comprises a support, a sample inlet port for deposition of a blood sample, and a reaction area comprising a blood coagulation reagent. The sample inlet port is connected to the reaction area, and the coagulation reagent comprises plasma deficient in the coagulation factor for which activity is to be measured, an ionic calcium source, an ionic citrate source, and either one or more coagulation contact phase activator reagents and phospholipids or a mixture of tissue factor and phospholipids. In the present invention "plasma" refers to blood plasma, which is the straw-colored/pale-yellow liquid component of blood that normally holds the blood cells in whole blood in suspension. It may be mostly water (92% by volume), and may contain dissolved proteins (i.e.—albumins, globulins, and fibrinogen), glucose, clotting factors, electrolytes (Na+, Ca2+, Mg2+, HCO3-CI– etc.), hormones and carbon dioxide (plasma being the main medium for excretory product transportation). Plasma is prepared by spinning a tube of fresh blood containing an anticoagulant in a centrifuge until the blood cells fall to the bottom of the tube.

In accordance with this aspect, a sample of whole blood (obtained by e.g. capillary puncture of a fingertip of a patient) may be introduced in the sample inlet port. The sample will reach the reaction area containing plasma deficient in the coagulation factor whose activity is going to be measured. By providing this plasma deficient in a specific factor (and importantly, normal amounts of the others), the amount of factor present in the patient's blood sample will become the reaction limiting element and thus the coagulation time will only be dependent of this variable. By measuring the coagulation time, the activity of the selected coagulation factor may be determined.

Thus, the proposed strips provide a way to correlate a clotting time with the corresponding percentage of activity of the clotting factor that is actually being measured.

A test strip is herein provided which may be combined with known equipment for determining coagulation time, such as the CoaguCheck Plus® mentioned before (or slightly modified versions thereof) to measure clotting factor activities. The equipment may be able to determine a change in phase based e.g. on IR emissivity/reflectivity or otherwise.

In case of coagulation factors linked to the extrinsic pathway of blood clotting, the coagulation reagent may comprise a mixture of tissue factor, calcium and phospholipids. In case of coagulation factors linked to the intrinsic pathway of blood clotting, the coagulation reagent may comprise coagulation contact phase activator, calcium and phospholipids. The coagulation reagent may be provided in e.g. dried or lyophilized form.

Inventors propose a test strip that allows measuring any coagulation factor deficiency using low amounts of whole blood, even of capillary blood.

The strips may thus easily be used as POC devices in hospitals or even by a patient in his or her house. The strips may even function well with low sample volumes. They may be portable and small sized. In addition, the strips may be manufactured using known and relatively simple procedures, thus implying low production costs.

Thus, they represent the provision of a long-felt need and they may improve not only a patient's quality of life, but may also improve diagnostic of diseases related to the impairment of coagulation pathways, such as haemophilia, by hospital personnel. Hence and of great interest, any therapeutic decision of administering or not a particular drug or coagulation factor may be reached in the shortest possible time.

In some embodiments, in the reaction area one or more of the ingredients is separated from another ingredient. The separation between ingredients may include a physical barrier (e.g. a wall of a compartment) or the (dried or lyophilized) ingredients may be immobilized in the reaction area at a distance from each other. One or more capillary tracks may be provided between compartments or ingredients to ensure proper mixture of ingredients, and in a predetermined order.

In some examples, the reaction area may comprise a first portion, a second portion, and third portion, the portions being substantially separated from each other, and the first portion comprises the plasma deficient in the coagulation factor for which activity is to be measured and an ionic citrate source, the second portion comprises one or more contact phase activator reagents and phospholipids, and the third portion comprises an ionic calcium source, A separation of the ingredients ensures that mixture may take place in a predetermined order. The order herein described is particularly suitable for factors involved in the intrinsic pathway. In another example, even the ionic citrate source may be in a separate portion, thus an additional portion may comprise the ionic citrate source separated from the plasma deficient in the coagulation factor for which activity is to be measured.

In some other examples, the reaction area may comprise a first portion and a second portion separated from each other, and the first portion comprises the plasma deficient in the coagulation factor for which activity is to be measured and an ionic citrate source, and the second portion comprises a mixture of an ionic calcium source, tissue factor and phospholipids. Such a test strip may be particularly suitable for factors involved in the extrinsic pathway. As above, in another example the ionic citrate source may be in a separate portion, thus an additional portion may comprise the citrate source separated from the plasma deficient in the coagulation for which activity is to be measured.

In some embodiments, the sample inlet port may be connected with the reaction area by a capillary track. Capillary tracks are known in the field of test strips. The separation of the sample inlet port from the reaction area ensures that clotting time may be reliably measured by determining a first phase change from solid to liquid (i.e. when blood of the patient's blood sample reaches the reaction area) and then from liquid to solid (i.e. when clotting has taken place).

In some embodiments, a test strip may further comprise a control fluid inlet port and a normal blood reaction area comprising blood or plasma containing standard (normal) known amounts of any of the coagulation factors (i.e. amounts correlating with or giving rise to an activity from 70% to 150%), wherein the second reaction area is connected to the control fluid inlet port, optionally through a capillary track.

Optionally, the test strip may furthermore or alternatively comprise a control fluid inlet port and a depleted blood reaction area comprising blood or plasma containing known levels (amounts) of the coagulation factor to be measured, said known levels of coagulation factor being lower than a reference value and/or out of a reference range, said reference value including standard (normal) amounts or ranges of activities (i.e. from 70% to 150%) and nonnormal but at the same time non-pathological activities (i.e. from 40% to 70%). By out of any reference values or range is to be understood that according to said reference ranges the value is a pathological one. In this specific case, it is a value lower than the lowest limit of the reference range. In a particular embodiment, the depleted blood reaction area comprises known levels of coagulation factor correlating with an activity being lower than 40%.

The provision of one or more further reaction areas comprising either blood/plasma with normal amounts of coagulation factor and blood/plasma with a relatively low amount of the coagulation factor to be measured may aid in improving the reliability of the measurements. The blood in these areas may be provided in dried or lyophilized form. The control fluid may be e.g. a physiological serum or buffer, or even distilled water in case the reaction areas comprise already buffered solutions. When the control fluid reaches the reaction area, a phase change from solid to liquid may be registered. When clotting occurs, a phase change from liquid to solid may then again be measured. Since the "amount" of the coagulation factor in these control areas is known, its coagulation time is known as well. It may thus be checked whether the coagulation time registered for the control areas coincides with the theoretical clotting time. If it does, one thus is able to conclude that the equipment used for measuring clotting is functioning properly. In a particular embodiment, reaction areas may be in the form of wells.

In some embodiments, the test strips may comprise a computer readable memory comprising data linking coagulation times that may be measured to activities of the coagulation factor to be measured. The data may e.g. be in the form of a coagulation curve or a look-up table indicating the activity level of a coagulation factor as a function of a coagulation time. Suitable equipment may read the memory and be able to indicate directly the level of activity of the coagulation factor under investigation. Coagulometers adapted for reading computer readable memory integrated in a test strip may be used.

In another aspect, an in vitro method for measuring an activity of a coagulation factor of the intrinsic or extrinsic pathway is provided. The method comprises contacting an isolated capillary blood sample from a test subject with a composition comprising a coagulation contact phase activator, a coagulation factor depleted plasma, an ionic citrate source, and an ionic calcium source, or alternatively, contacting the sample with a mixture of tissue factor and phospholipids, a coagulation factor depleted plasma, an ionic citrate source, and an ionic calcium source; determining the time required for coagulation of said sample; and correlating said coagulation time with a particular activity by comparison with a coagulation function, said the coagulation function representing the relation between coagulation time and the activity of a coagulation factor.

In some embodiments, the method may be used for rendering a diagnosis wherein, if the time required for coagulation is higher than a reference value or range from subjects with no coagulation factor deficiency, it is indicative of pathological coagulation factor deficiency. The reference value or reference range is in particular the time or range of times correlating with nonpathologic activities. Such a reference may include normal values and also non-normal values but considered non-pathological for a particular coagulation factor. Thus, if the time required for coagulation is higher than a reference value or range, this means that the activity of the factor is lower than the reference value and, it is indicative of pathological coagulation factor deficiency.

In a particular embodiment, the activity of the coagulation factor is lower than 40% in case of a deficiency of any of the tested coagulation factors.

The method may also be used for diagnosing non-normal and at the same time non-pathological activities of a particular coagulation factor. This is the particular case when the activity detected is in the range of values from 40% to 70%. Although it depends on the tested factor, for most of them this range of activities is indicative of coagulation factor deficiency (not normal amounts; 70%-150%) but of non-pathological kind. Determination of non-normal but non-pathological activities of a factor allows deciding on a particular medical treatment including the follow-up of the patient without treatment.

In a particular example of the in vitro diagnosis method of the invention, the coagulation factor deficiency is selected from the group consisting of deficiencies of coagulation Factor V (FV), deficiencies of coagulation Factor VII (FVII), deficiencies of coagulation Factor VIII (FVIII), the deficit or deficiency of which causes hemophilia A, deficiencies of coagulation Factor IX (FIX) the deficit or deficiency of which causes hemophilia B, deficiencies of coagulation Factor X (FX), deficiencies of coagulation Factor XI (FXI), and deficiencies of coagulation Factor XII (FXII).

These deficiencies may be congenital or me be acquired coagulopathies (deficiencies) of different origins. Illustrative examples include coagulation factor synthesis deficiencies or inhibition such as in anticoagulant therapy (heparin, low molecular weight heparins, warfarin, coumarin derivatives, dicoumarins, etc.), or in severe hepatic failure or presence of acquired inhibitors. Acquired coagulopathies leading to coagulation factor deficiencies may be due to an exaggerated consumption of coagulation factors, thus making them not available to form the clot in a bleeding lesion. This mechanism occurs for example in the disseminated intravascular coagulation syndrome due to consumption occurring in multiple illnesses such as in severe sepsis, wherein the formation of multiple microthrombi diminishes the levels of coagulation factors. Another example is in blood invasion by tissue factor such as placental release; in the retention of a dead fetus; in multiple traumas with the crushing of tissues; in poisonous snake bites, etc. In all these diseases or conditions, the consumption of coagulation factors is worsened by lysis of the fibrin of numerous microthrombi due to the action of plasmin, which are antiplatelets and anticoagulants.

In a particular example of the method, step (i) is carried out by contacting an isolated capillary blood sample from a test subject with a composition comprising a coagulation contact phase activator, a coagulation factor depleted plasma, an ionic citrate source, and an ionic calcium source. This embodiment allows the determination of the activity of a coagulation factor of the intrinsic pathway. In another particular example of the method for measuring the activity of a coagulation of the intrinsic pathway, step (i) may be carried out by:
  (a) first contacting an isolated capillary blood sample from a test subject with a composition comprising a coagulation factor depleted plasma and an ionic citrate source to obtain a primary mixture;
  (b) further contacting the primary mixture of step (a) with a coagulation contact phase activator, an ionic calcium source and phospholipids; and
  (c) contacting the mixture of step (b) with an ionic calcium source.

In some embodiments, step (b) may be performed at a temperature from approximately 35° C. to 39° C. and for a time from 15 seconds to 5 minutes. It is in step (b) that the mixture contacts the reagents known as APTT reagents. In some other embodiments, optionally in combination with any embodiment described further below or above, step (c) may be carried out at temperature from 35° C. to 39° C. Particular examples of coagulation factors of the intrinsic pathway which activity may be determined by this method include factor VIII, IX, XI and XII.

All these steps (a) to (c) may be performed in a test strip provided with a reaction area with multiple compartments. In each compartment there may be provided the compounds or compositions in lyophilized or liquid form. Mixture of the sample with the compounds or compositions may be achieved capillarity.

In a particular example of the method, step (i) may be carried out by contacting an isolated capillary blood sample from a test subject with a composition comprising a mixture of tissue factor and phospholipids, a plasma deficient in the coagulation factor for which activity is to be measured, an ionic citrate source, and an ionic calcium source.

This embodiment allows the determination of the activity of a coagulation factor of the extrinsic pathway. In another particular example of the method for measuring the activity of a coagulation of the extrinsic pathway, step (i) may be carried out by:
  (a) first contacting an isolated capillary blood sample from a test subject with a composition comprising a coagulation factor depleted plasma and an ionic citrate source to obtain a primary mixture; and
  (b) further contacting the primary mixture of step (a) with a mixture of tissue factor and phospholipids, an ionic calcium source and phospholipids.

In an embodiment, step (b) may be performed at a temperature from 35° C. to 39° C. This step (b) is, the step in which the mixture of step (a) enters into contact with the known PT reagents. Particular examples of coagulation factors of the extrinsic pathway which activity may be determined by this method include factor II, V, VII and X.

All these steps (a) to (b) may be performed in a test strip provided with a reaction area with multiple compartments. In each compartment the compounds or compositions may be provided in lyophilized or liquid form. Mixture of the sample with the compounds or compositions may be achieved, by capillarity.

In any of the examples of the method, the step (ii) of determining the time required for blood coagulation, may start when in any of the options the sample (or mixtures) enter into contact with the calcium source. Afterwards, the method may include step (iii) of correlating blood coagulation time with a particular activity.

Any of the methods hereinbefore described allows detecting if a subject is suffering from any coagulation factor deficiency using low volume samples (capillary blood) in contrast with the prior art tests.

Additional objects, advantages and features of the invention will become apparent to those skilled in the art upon examination of the description or may be learned by practice of the invention.

BRIEF DESCRIPTION OF THE DRAWINGS

Particular embodiments of the present invention will be described in the following by way of non-limiting examples, with reference to the appended drawings, in which.

DETAILED DESCRIPTION

Figure 1A:
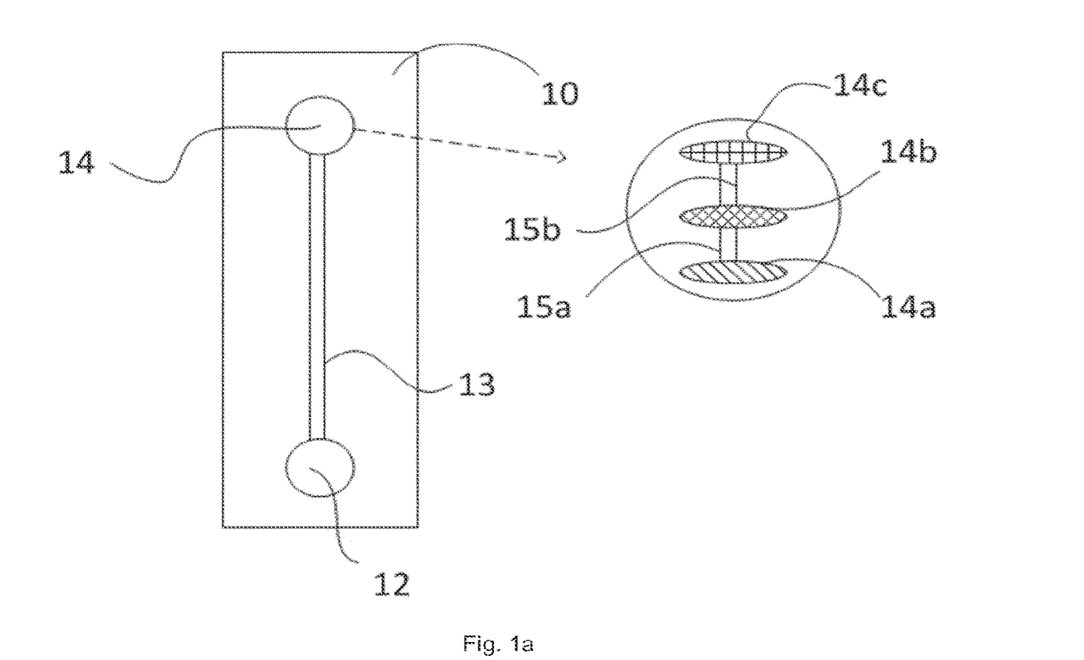
FIGS. 1*a* and 1*b* schematically illustrate top views of different examples of test strips.

FIG. 1*a* schematically illustrates a top view of a test strip according to a first example. A strip 10 may comprise a support in which a sample inlet port 12 is provided. Also a reaction area 14 is indicated. A track 13 may connect the sample inlet port with the reaction area 14.

The track 13 may be a capillary track. In alternative examples, the transport of the blood sample from the deposition area 12 to the reaction area 14 may be based on a different principle, such as e.g. pumping or suction. The support may comprise one or more layers of semi-rigid plastic. A top layer may be provided that closes off the reaction area and/or the deposition area from the top. A patient, doctor or laboratory personnel staff may deposit a drop or few drops of whole blood in the deposition area 12 (e.g. after uncovering). In one possible implementation, the blood may have been extracted through a capillary puncture in the fingertip.

The layers may be made suitable for the measurement method employed. For example, they may be substantially transparent or translucent if the method for determining clotting is based on e.g. light absorption/reflection. If the measurement method is based on e.g. an electrical characteristic (such as e.g. the impedance), suitable materials may be chosen and a suitable electric circuit may be provided in the support.

The reaction area may comprise blood coagulation reagent which may vary depending on the clotting factor to be investigated. The clotting factor (or "blood coagulation factor") for which the activity is measured may be selected from the group consisting of factor II, V, VII, X, VIII, IX, XI and XII.

Depending on the factor to be investigated, the blood coagulation reagent may comprise plasma deficient in the selected coagulation factor, an ionic calcium source and either one or more coagulation contact phase activator reagents and phospholipids (for factors related to the intrinsic pathway) or a mixture of tissue factor and phospholipids (for factors related to the extrinsic pathway).

The coagulation contact phase activators may be selected from the group consisting of polyanionic compounds, organic acids and mixtures thereof. The calcium source may be a calcium salt selected from the group consisting of calcium chloride, calcium acetate, calcium carbonate, calcium glubionate, calcium gluconate, calcium hydroxide, calcium nitrate, calcium sulfonate, calcium phosphate, and mixtures of these salts. The ionic citrate source may be sodium citrate and/or acid-citrate-dextrose. In a preferred embodiment the ionic citrate source is sodium citrate.

The coagulation reagent may be in liquid, semi-solid or solid form. The coagulation reagent may be lyophilized. Alternatively, the coagulation reagent may be otherwise immobilized in the reaction area. Once the whole blood sample of the patient reaches the reaction area, a local change may be measured, in particular in the case of a lyophilized reagent, a phase change from solid to liquid may be measured. When a phase change from liquid to solid is registered coagulation has taken place. The coagulation time may thus be derived from the time passed between the first change and the second change. Other known methods for determining coagulation times may also be used.

Any suitable equipment such as a coagulometer for this sort of determination may be used and may be based e.g. on optical principles (reflexivity/emissivity), mechanics, inductance, electric resistance or impedance and other (or combinations thereof). In some examples, portable coagulometers may be used. The test strip may be introduced into the coagulometer either before or after deposition of the whole blood sample. The dimensions of the test strip may be determined in accordance with the equipment used for analysis.

FIG. 1*a* further illustrates an example of how ingredients of the coagulation reagents may be separated in a reaction area. In the schematically illustrated example, the reaction area may comprise a first portion 14*a*, a second portion 14*b*, and a third portion 14*c*.

The portions 14*a*, 14*b* and 14*c* may be substantially separated from each other: this may be achieved e.g. by creating separate compartments. Separate compartments may be particularly useful when the ingredients are provided in liquid form. In another example, the ingredients may be provided in dried or lyophilized form. If properly immobilized, separate compartments may not be necessary.

In this particular example, the first portion may comprise the plasma deficient in the coagulation factor for which activity is to be measured and an ionic citrate source. The second portion may comprise one or more contact phase activator reagents and phospholipids, and the third portion may comprise an ionic calcium source, A separation of the ingredients ensures that mixture may take place in a predetermined order. Capillary tracks 15*a* and 15*b* connect the separate portions. The length of the capillary track may determine the time it takes for the mixture to reach a next portion. In this sense, proper dimensioning of the capillary track can ensure that mixture of ingredients take place before the next ingredient is reached. In other examples, other mechanisms such as suction or pumping may be used to connect the separate ingredients. The order described in this example is particularly suitable for factors involved in the intrinsic pathway.

In an alternative-non-illustrated example, two separate portions could be provided for the extrinsic pathway factors. The first portion in such an example may comprise the plasma deficient in the coagulation factor for which activity is to be measured and an ionic citrate source, and the second portion may comprise an ionic calcium source and a mixture of tissue factor and phospholipids.

Figure 1B:
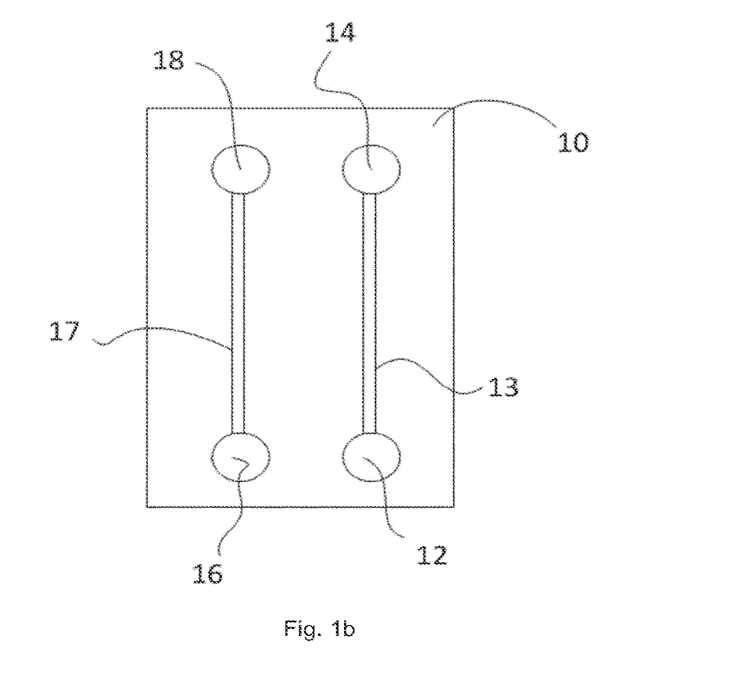

FIG. 1b illustrates another example of a test strip 10. The test strip comprises a sample deposition area 12, track 13 and reaction area 14 similar to the one showed in the example of FIG. 1a. Additionally, the strip in this example may comprise a control fluid deposition area 16, and a track 17 connecting the deposition area 16 with a control reaction area 18.

The control reaction area 18 may comprise a lyophilized blood or plasma sample of known composition. In an example, the blood or plasma sample may comprise normal amounts of the coagulation factors (i.e. with activities from 70% to 150%) or alternatively the blood or plasma sample may have a relatively low known amount of the coagulation factor to be investigated, being said relatively low known amount an amount (or level of coagulation factor) lower than and out of any normal amount or range of normal amounts (i.e. with activities of 70%-150%), or lower than and out of a non-normal and non-pathological amount or range (i.e. with activities from 40% to 70%). Thus, in another example, the blood or plasma sample may have an amount of coagulation factor activity lower than 40%. This means that the factor activity of the blood control sample is lower than 40%, which reflects a pathological value.

In some examples, the control reaction area(s) may comprise a mixture of blood or plasma with a known amount of coagulation factor, a citrate source, one or more contact phase activator reagents and phospholipids, and an ionic calcium source. Such an example may be suitable for factors involved in the intrinsic pathway. In some other examples more suitable for the extrinsic pathway factors, the control reaction area(s) may comprise a mixture of blood or plasma with a known amount of coagulation factor, a citrate source, an ionic calcium source and a mixture of tissue factor and phospholipids.

Figure 1C:
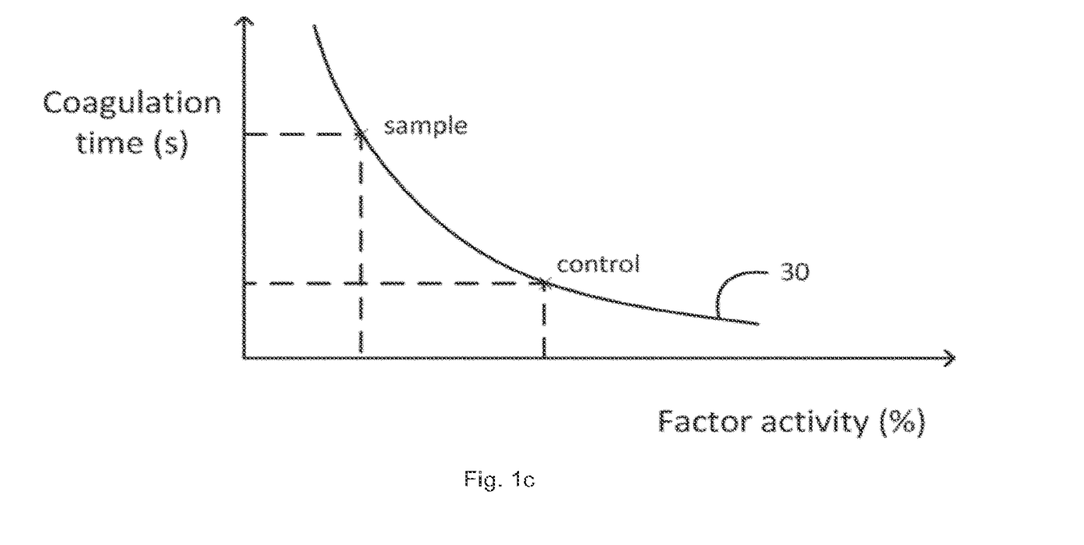
FIG. 1*c* schematically illustrates a coagulation curve which may be used in combination with the example of FIG. 1*b*.

In either case, the control reaction area may serve to check or confirm the results obtained in the reaction area. Reference may be had to FIG. 1c schematically illustrating a coagulation curve 30 showing the relation between coagulation time and a level of activity of a specific coagulation factor.

In some examples, a similar separation of ingredients as illustrated in FIG. 1a for the reaction area may be used in such a control reaction area. A first portion could comprise the blood or plasma with normal amounts of coagulation factor and the citrate source; or blood or plasma with a relatively low amount of the coagulation factor and the citrate source. If the coagulation factor to be measured is from the intrinsic pathway, the second portion may comprise one or more contact phase activator reagents and phospholipids, and the third portion may comprise an ionic calcium source. If the coagulation factor to be measured is from the extrinsic pathway, with two portions may be enough and said second portion may comprise an ionic calcium source and a mixture of tissue factor and phospholipids. As explained above for the reaction area, separate compartments may be particularly useful when the ingredients of control areas are provided in liquid form. In another example, the ingredients may be provided in dried or lyophilized form. If properly immobilized, separate compartments may not be necessary while still maintaining separation between different ingredients.

With this kind or pattern of ingredient distribution in the control reaction areas the method of the invention may be accomplished in the same experimental conditions as in the reaction area, wherein the sample of the patient is going to be tested. That is, in the same order, and same incubation times with the particular ingredients. If the ingredients in the control reaction areas are in dried or lyophilized form, they are rehydrated or allowed to evolve to a liquid form with the control fluid (physiological serum or buffer, or even distilled water in case the reaction areas comprise already buffered solutions).

In an example, the control fluid may be a physiological serum, or a physiological buffer of some kind. Through e.g. capillary action, the control fluid may reach the control reaction area 18 and may bring about a phase change from solid to liquid. After clotting, a phase change from liquid to solid may occur. Since the amount of the coagulation factor in the control sample is known, its theoretical coagulation time which should lie on coagulation curve 30 is known as well. If in a test it is found that the control sample factor activity indeed lies within some previously established limits considered acceptable then this is an indication that the test equipment is working properly. If on the other hand, a deviation from those limits is found, this may indicate a malfunction of some sort.

Alternatively to a coagulation curve such as the one illustrated in FIG. 1c, the relation between clotting time and level of activity of the coagulation factor may be stored in alternative manners, e.g. in the form of a look-up table or in the form of a mathematical equation.

Figure 2A:
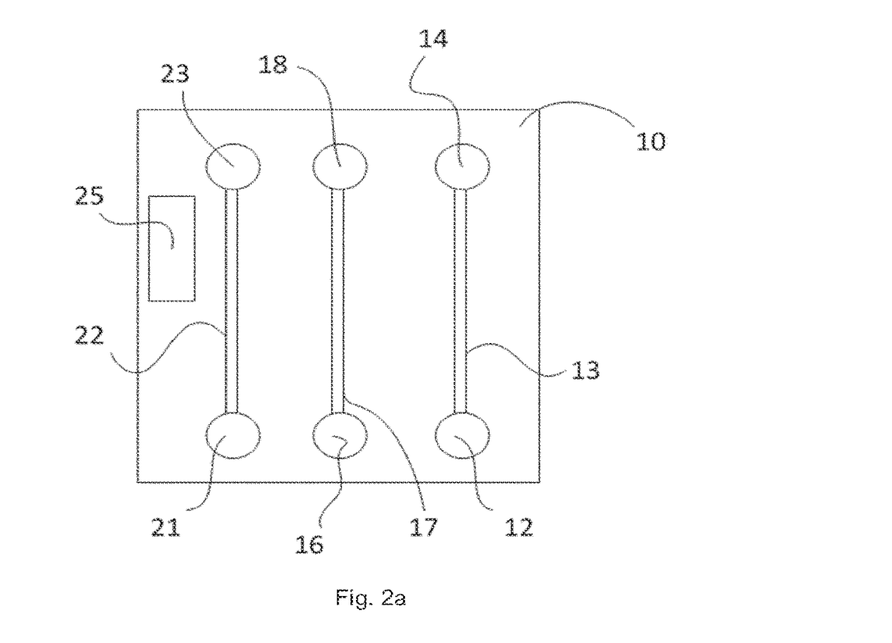
FIG. 2*a* schematically illustrates a top view of another example of a test strip.

FIG. 2a schematically illustrates a further example of a test strip 10. In this example, three capillary tracks may be arranged. A sample inlet port 12 may be connected to a reaction area 14 via a capillary track 13. A first control fluid inlet port 16 may be connected to a first control reaction area 18 via a capillary track 17. A second control fluid inlet port 21 may be connected to a second control reaction area 23 via a capillary track 22.

The first control reaction area 18 may be a standard blood reaction area comprising blood containing a known normal amount of the coagulation factor whose activity is to be measured, and also including normal amounts of any of the other coagulation factors.

The second control reaction area 23 may be a depleted blood reaction area comprising blood with a relatively low (but known) amount of the coagulation factor to be measured and substantially normal amounts of the other coagulation factors. The relatively low known amount is an amount (or level of coagulation factor) lower than and out of any normal amount or range of standard amounts. Thus, in another example, the depleted blood reaction area may comprise blood with an amount of coagulation factor with an activity lower than 70%. This means that the activity of the blood control sample is lower than 70%.

Schematically illustrated is a chip 25 comprising a computer readable memory. The memory may be read by suitable equipment, e.g. the same equipment used for determining the clotting time.

A control fluid may be deposited in the control fluid inlet ports or areas 16 and 21. Substantially at the same time a blood sample may be deposited in the sample inlet port 12. The reaction strip may then be inserted into suitable laboratory equipment capable of determining clotting and capable of reading chip 25. Alternatively and depending on the equipment used, the strip may have been inserted into the equipment prior to deposition of the sample and control fluid.

Once the blood sample reaches the reaction area, clotting may begin. Once the control fluid reaches the control reaction areas, the lyophilized samples may change from a solid state to a liquid state and then clotting may begin in the reaction areas. Other known methods for determining coagulation times may also be used.

Figure 2B:
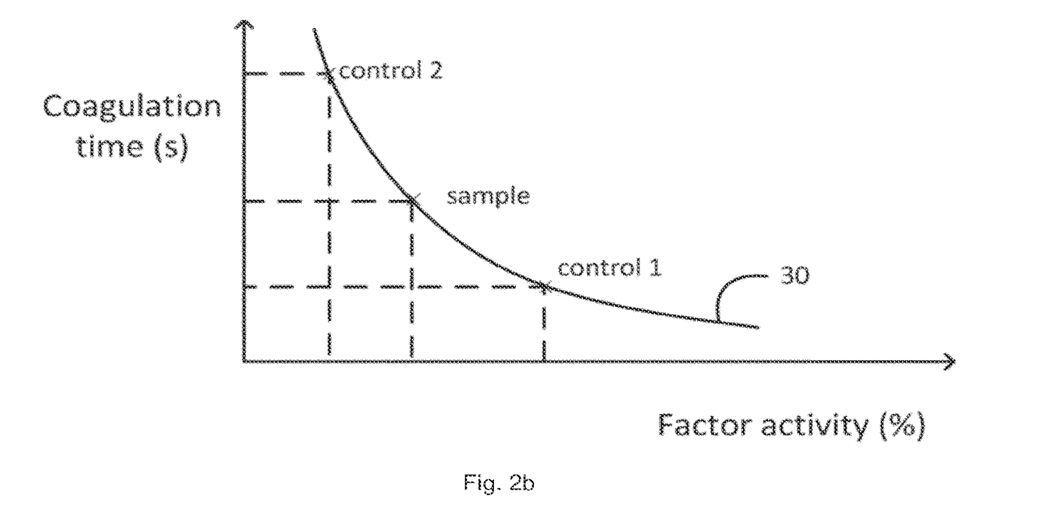
FIG. 2*b* schematically illustrates a coagulation curve which may be used in combination with the example of FIG. 2*a*.

In accordance with FIG. 2b, in a single strip a reliable indication of the level of activity of the coagulation factor may be found. The clotting times found in the two control reaction areas are expected to lie between previously established acceptability limits. This curve and information on the composition of the samples in areas 18 and 23 may be stored in the memory of chip 25. If the clotting times found in the control areas both lie within the limits, it may be confirmed that the laboratory equipment and reagents used in functioning correctly and that the test strip is not defective.

The clotting time found in the reaction area 14 may thus reliably indicate the level of activity of the coagulation factor being investigated.

Alternatively to storing the coagulation curve (or similar data) on a chip incorporated in the test strip, the information may be previously stored in the laboratory equipment used. In yet a further alternative, for each manufacturing batch of test strips, a single test strip with such a chip or computer readable memory may be provided. The readings from this chip may be held to be representative for the complete batch, as it may be assumed that a manufacturing batch will generally comprise the same or very similar lyophilized blood samples and/or reagents in each strip.

Figure 3:
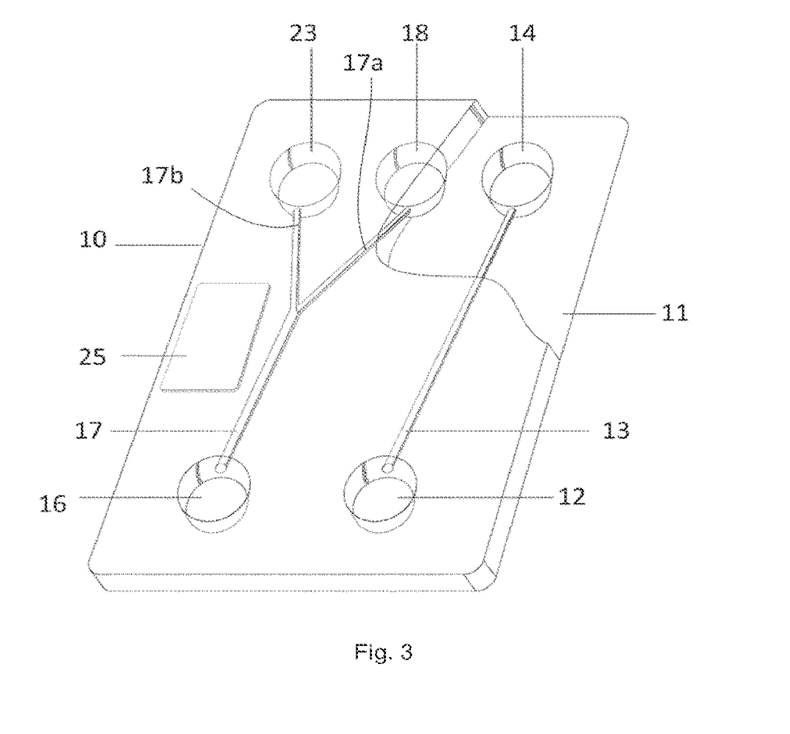
FIG. 3 is a schematic perspective view of the strip according to yet another example.

FIG. 3 illustrates a further alternative example of a test strip. The principles upon which this example is based are largely the same as those illustrated and explained with reference to FIGS. 2a and 2b. However, a single control fluid inlet port 16 is connected by a bifurcated track or channel 17 which leads to two control reaction areas through partial channels 17a and 17b. As in the previously illustrated example, the first control reaction area 18 may comprise blood containing a normal amount of the coagulation factor for which activity is to be measured and the second control reaction area 23 may be a depleted blood reaction area comprising blood with a relatively low amount of the coagulation factor to be measured.

Throughout the description and claims the word "comprise" and variations of the word, are not intended to exclude other technical features, additives, components, or steps. Furthermore, the word "comprise" encompasses the case of "consisting of".

Although only a number of particular embodiments and examples of the invention have been disclosed herein, it will be understood by those skilled in the art that other alternative embodiments and/or uses of the invention and obvious modifications and equivalents thereof are possible. Furthermore, the present invention covers all possible combinations of the particular embodiments described. Thus, the scope of the present invention should not be limited by particular embodiments, but should be determined only by a fair reading of the claims that follow.

The invention claimed is:

1. A cartridge comprising:
   (a) a sample inlet port configured to receive a blood sample;
   (b) a first compartment configured to receive at least a portion of said blood sample from said sample inlet port, wherein said first compartment contains an ionic citrate source configured to produce citrated blood upon contacting said at least said portion of said blood sample; and
   (c) a second compartment that contains a depleted plasma that is depleted of a coagulation factor, wherein said second compartment is in fluidic communication with said first compartment and is configured to receive at least a portion of said citrated blood.

2. The cartridge of claim 1, wherein said depleted plasma is lyophilized.

3. The cartridge of claim 1, wherein said depleted plasma is depleted of at least one of: Factor II, Factor V, Factor VII, Factor VIII, Factor IX, Factor X, Factor XI, and Factor XII.

4. The cartridge of claim 1, further comprising a third compartment that contains a coagulation contact phase activator, wherein said second compartment is in fluidic communication with said third compartment and is configured to receive at least a portion of said coagulation contact phase activator from said third compartment.

5. The cartridge of claim 4, wherein said third compartment further contains a calcium source, a Tissue Factor, a phospholipid, or any combination thereof.

6. The cartridge of claim 1, wherein said second compartment further contains a calcium source, a Tissue Factor, a phospholipid, or any combination thereof.

7. The cartridge of claim 1, further comprising a capillary configured to fluidically connect said first compartment and said second compartment.

8. The cartridge of claim 4, further comprising a capillary configured to fluidically connect said first compartment and said third compartment.

9. The cartridge of claim 1, further comprising a reference compartment, wherein said reference compartment contains a reference sample.

10. The cartridge of claim 9, wherein said reference sample is a plasma containing said coagulation factor.

11. The cartridge of claim 9, wherein said reference sample is lyophilized.

12. A system comprising said cartridge of claim 1 and a detector.

13. The system of claim 12, wherein said detector comprises an imaging detector.

14. The system of claim 12, wherein said cartridge is configured to communicate with said detector.

15. The cartridge of claim 1, wherein said ionic citrate source comprises sodium citrate.

16. The cartridge of claim 1, wherein said ionic citrate source comprises acid-citrate-dextrose.

17. The cartridge of claim 5, wherein said calcium source comprises a calcium salt.

18. The cartridge of claim 17, wherein said calcium salt comprises calcium chloride, calcium acetate, calcium carbonate, calcium glubionate, calcium gluconate, calcium hydroxide, calcium nitrate, calcium sulfonate, calcium phosphate, or a mixture thereof.

19. The cartridge of claim 6, wherein said calcium source comprises a calcium salt.

20. The cartridge of claim 19, wherein said calcium salt comprises calcium chloride, calcium acetate, calcium carbonate, calcium glubionate, calcium gluconate, calcium hydroxide, calcium nitrate, calcium sulfonate, calcium phosphate, or a mixture thereof.

21. The cartridge of claim 4, wherein said coagulation contact phase activator comprises a polyanionic activator, a kaolin, an organic acid, or a mixture thereof.

22. The cartridge of claim 21, wherein said coagulation contact phase activator comprises said polyanionic activator.

23. The cartridge of claim 21, wherein said coagulation contact phase activator comprises said kaolin.

24. The cartridge of claim 21, wherein said coagulation contact phase activator comprises said organic acid.

25. The cartridge of claim 24, wherein said organic acid comprises an ellagic acid.

\* \* \* \* \*